United States Patent
Taniguchi et al.

(10) Patent No.: US 7,868,618 B2
(45) Date of Patent: Jan. 11, 2011

(54) MAGNETIC RESONANCE IMAGING APPARATUS

(75) Inventors: Yo Taniguchi, Kokubunji (JP); Hisaaki Ochi, Kodaira (JP)

(73) Assignee: Hitachi Medical Corporation, Tokyo (JP)

(*) Notice: Subject to any disclaimer, the term of this patent is extended or adjusted under 35 U.S.C. 154(b) by 113 days.

(21) Appl. No.: 12/308,186

(22) PCT Filed: Jun. 12, 2007

(86) PCT No.: PCT/JP2007/061780
§ 371 (c)(1),
(2), (4) Date: Dec. 9, 2008

(87) PCT Pub. No.: WO2007/145193
PCT Pub. Date: Dec. 21, 2007

(65) Prior Publication Data
US 2009/0251142 A1    Oct. 8, 2009

(30) Foreign Application Priority Data
Jun. 16, 2006    (JP) .............................. 2006-167868

(51) Int. Cl.
*G01V 3/00* (2006.01)
(52) U.S. Cl. ...................................... 324/318; 324/322
(58) Field of Classification Search ......... 324/300–322; 600/407–445
See application file for complete search history.

(56) References Cited
U.S. PATENT DOCUMENTS
| 4,808,928 | A  | * | 2/1989 | Frahm et al. ................. 324/309 |
| 5,307,015 | A  | * | 4/1994 | Kaufman et al. ............. 324/309 |
| 6,291,996 | B1 | * | 9/2001 | Glover et al. ............... 324/309 |
| 7,367,155 | B2 | * | 5/2008 | Kotyk et al. ................... 47/14 |
| 7,403,006 | B2 | * | 7/2008 | Garwood et al. ............ 324/310 |
| 7,425,828 | B2 | * | 9/2008 | Garwood et al. ............ 324/310 |

(Continued)

FOREIGN PATENT DOCUMENTS
DE    10 2004 031 204 A1    6/2004

(Continued)

OTHER PUBLICATIONS

Paul et al: T2-weighted b-SSFP Imaging Using TIDE; Proc. Intl. Soc. Mag. Reso. Med vol. 13 (2005).*

*Primary Examiner*—Brij B Shrivastav
(74) *Attorney, Agent, or Firm*—Antonelli, Terry, Stout & Kraus, LLP.

(57) ABSTRACT

The MRI apparatus of the present invention executes a non-imaging mode 501 for obtaining a steady state of magnetization and an imaging mode 502 for measuring echoes for images. In the non-imaging mode 501 and the imaging mode 502, imaging is performed by using a GrE type pulse sequence. In the imaging, RF pulses are irradiated while flip angle of nuclear magnetization in the imaging mode 502 is changed in a range of values not larger than a certain value determined by flip angle of nuclear magnetization used in the non-imaging mode 502 is irradiated. This certain value is, for example, the maximum value of flip angle of nuclear magnetization used in the non-imaging mode, or flip angle provided by an RF pulse used at the end of the non-imaging mode. SAR observed with use of a GrE type pulse sequence can be thereby reduced without degrading image contrast, and thus influence on human bodies can be reduced.

12 Claims, 9 Drawing Sheets

U.S. PATENT DOCUMENTS

| | | | |
|---|---|---|---|
| 7,777,484 B2 * | 8/2010 | Garwood et al. | 324/307 |
| 7,800,368 B2 * | 9/2010 | Vaughan et al. | 324/318 |
| 2005/0001617 A1 | 1/2005 | Busse | |
| 2005/0122103 A1 | 6/2005 | Le Roux | |
| 2005/0240095 A1 | 10/2005 | Schaffter | |
| 2008/0080775 A1 * | 4/2008 | Zabih et al. | 382/226 |
| 2010/0085050 A1 * | 4/2010 | Dong et al. | 324/309 |

FOREIGN PATENT DOCUMENTS

| | | |
|---|---|---|
| DE | 10 2004 005 174 A1 | 8/2004 |
| FR | 2 851 050 | 2/2003 |
| JP | 03-133427 | 6/1991 |
| JP | 09-262220 | 10/1997 |
| JP | 2004-237102 | 8/2004 |
| JP | 2005-021690 | 1/2005 |
| NL | 1025389 | 2/2004 |

\* cited by examiner (a)

(b)

MAGNETIC RESONANCE IMAGING APPARATUS

TECHNICAL FIELD

The present invention relates to a magnetic resonance imaging technique.

BACKGROUND ART

Nuclear magnetic resonance imaging (MRI) apparatuses are diagnostic imaging apparatuses for medical use that induce nuclear magnetic resonance in nuclei of hydrogen atoms contained in an arbitrary plane traversing a test subject, and produce a tomographic image of a region in the plane using generated nuclear magnetic resonance signals. In general, when a slice magnetic field gradient for specifying imaging slice is applied, an excitation pulse is applied in order to excite magnetizations in the plane at the same time. Nuclear magnetic resonance signals (echoes) generated in the course of the precession of the magnetizations excited by the pulses. Positional information is imparted to the echoes by the magnetic field gradient, and Fourier transform of the echoes is performed to reconstruct images. The angle of inclination of the magnetization with respect to the direction of the static magnetic field, i.e., flip angle, is determined by time integration value of amplitude of the excitation pulse, and an angle providing appropriate image contrast is chosen according to the imaging method.

The pulse and magnetic field gradients used for generating echoes are applied according to a predefined pulse sequence. As for the pulse sequence, various pulse sequences are known in association with different purposes. For example, a gradient echo (GrE) type high-speed imaging method is a method in which such a pulse sequence is repeatedly executed, and the phase-encoding magnetic field gradient is sequentially changed for every repetition to sequentially measure echoes in a number required for obtaining one tomographic image.

Another GrE type pulse sequence is a phase compensation type pulse sequence. In this pulse sequence, a magnetic field gradient pulse for making the time integration value of the magnetic field gradient for each axis is added to GrE. Degree of the flip angle is generally larger than that used in the GrE method, and the phase thereof is reversed in every execution. Moreover, the repetition time TR is shorter, and is around 5 ms.

In such a GrE type imaging method, before execution of a pulse sequence for measuring echoes required for image reconstruction (imaging mode), magnetization is repeatedly excited in order to obtain a steady state of magnetization. This procedure is called non-imaging mode. In the non-imaging mode, the same pulse sequence as that used in the imaging mode is executed a predetermined number of times without measuring echoes. However, in order to obtain a steady state of magnetization with less times of excitation, the flip angle in the non-imaging mode may be gradually increased from a small angle and made closer to the angle used in the imaging mode.

Moreover, in these high-speed imaging methods, the flip angle greatly influences image contrast. Therefore, an angle providing a certain degree of image contrast is generally chosen from the range of 10 to 90 degrees as the flip angle for the imaging mode, and the flip angle is not usually changed during a period for obtaining one image.

In MRI, the magnetic resonance frequency becomes higher in proportion to the magnetic field intensity. In connection with this fact, there arises a problem of increase in absorption of RF electric power into human bodies, called specific absorption rate (SAR), and development of countermeasure against it constitutes a subject of researches. SAR is RF irradiation power per unit time, and it is proportional to the time integration value of square of the flip angle and is in inverse proportion to TR. The reference value of the maximum thereof for human body is defined to be 4 W/kg. When a GrE type pulse sequence is used, RF irradiation is repeated in a short time, and therefore SAR becomes large. In particular, phase compensation type GrE pulse sequences use a short TR and a large flip angle, and therefore it is difficult to apply such sequences to a human body in a high magnetic field apparatus using a magnetic field of about 3 Teslas or more in view of safety. For example, for a case that a phase compensation type GrE pulse sequence using a flip angle of 60 degrees and TR of 3 ms is executed in an apparatus using a magnetic field of 3 Teslas, SAR is calculated to be 4.7 W/kg. This value exceeds the reference value, and therefore it is impossible to perform imaging.

To solve this problem, there has been proposed a method of changing flip angle of RF excitation pulse for the imaging mode according to the amount of phase encoding so that image contrast should not be degraded, in consideration of the specific absorption rate SAR (henceforth this method is referred to as prior art 1, Patent document 1). This method is based on the fact that image contrast in MRI is generally determined by contrast of echoes having a small phase encoding amount, and the flip angle is made large when the phase encoding amount is small, so that image contrast should not be degraded even when the flip angle is changed.

Patent document 1: Japanese Patent Unexamined Publication (KOHYO) No. 2005-524453

DISCLOSURE OF THE INVENTION

Object to be Achieved by the Invention

In the aforementioned prior art 1, the non-imaging mode is not taken into consideration at all. However, according to the researches of the inventors of the present invention, in the case of a GrE type pulse sequence, the major factor determining contrast provided by an echo is not a flip angle of the RF pulse which generated the echo, but a steady state formed in the non-imaging mode. Therefore, even if only flip angle of an RF pulse for generating an echo having a small phase encoding amount is made large according to the prior art 1, intended image contrast may not necessarily be obtained.

The object of the present invention is to reduce SAR with a given GrE type pulse sequence without degrading image contrast, and thereby provide an MRI apparatus which can reduce the influence on human bodies.

Means for Achieving the Object

According to the present invention, in order to achieve the aforementioned object, SAR is reduced without degradation of image contrast by changing the flip angle within a range of values not larger than a certain value in the imaging mode using a GrE type pulse sequence. The certain value serving as the upper limit of the flip angle in the imaging mode is defined by the flip angle used in the non-imaging mode.

That is, the MRI apparatus of the present invention comprises a means for generating a static magnetic field, a means for generating a magnetic field gradient to be superimposed on the static magnetic field, a means for irradiating an excitation RF pulse on a test subject placed in the static magnetic field, a means for detecting nuclear magnetic resonance signals emitted from the test subject, a means for reconstructing an image from the nuclear magnetic resonance signals, and a means for controlling the means for irradiating an excitation RF pulse and the means for detecting nuclear magnetic resonance signals so as to execute a non-imaging mode in which nuclear magnetic resonance signal is not measured after irradiation of an excitation RF pulse, and an imaging mode in which a nuclear magnetic resonance signal is measured after irradiation of an excitation RF pulse, wherein the means for irradiating an excitation RF pulse changes flip angle of nuclear magnetization in the imaging mode in a range of values not larger than a certain value defined by a flip angle of nuclear magnetization used in the non-imaging mode.

The certain value is, for example, the maximum value of the flip angle of the nuclear magnetization used in the non-imaging mode. Alternatively, it is the flip angle of the nuclear magnetization at the time of the end of the non-imaging mode. While the changing manner of the flip angle (modulation pattern) in a range of values not larger than a certain value may be any of various manners such as monotone decreasing, and combination of monotone decreasing and monotone increasing, the change is preferably substantially continuous change.

Moreover, in the MRI apparatus of the present invention, the means for reconstructing an image preferably comprises a means for correcting the nuclear magnetic resonance signals measured in the imaging mode according to flip angle of the excitation RF pulse used in order to generate the nuclear magnetic resonance signals.

EFFECT OF THE INVENTION

According to the present invention, it becomes possible to obtain image contrast comparable to that obtainable with a constant flip angle, while preventing the heating effect by RF pulse irradiation, by maintaining the flip angle to be not larger than a certain value.

SAR corresponds to RF irradiation power per unit time. Therefore, in order to reduce SAR, it is necessary to lengthen the repetition time TR or to make the flip angle small. However, it is not preferable to change TR, since TR strongly affects the contrast of water and fat. Therefore, the flip angle is made small. In this case, if the flip angle is simply made small, contrast is degraded. Therefore, the flip angle is modulated within a range of values not larger than a flip angle providing desired image contrast as the upper limit to reduce SAR with maintaining image contrast.

In particular, when an imaging method includes execution of a non-imaging mode, image contrast is determined by a steady state attained in the non-imaging mode. Therefore, by defining the maximum value of the flip angle of magnetization (certain value) used in the imaging mode with the flip angle used in the non-imaging mode, an image can be obtained with favorable image contrast. This SAR reducing effect is especially more significant for a phase compensation type GrE pulse sequence using a large flip angle and short TR.

Moreover, a means for correcting influence of the modulation of the flip angle on image quality may be used in the present invention, and this enables provision of an image of still more favorable image quality.

BEST MODE FOR CARRYING OUT THE INVENTION

Hereafter, examples of the present invention will be explained in detail with reference to the drawings.

FIG. 1 is a block diagram showing outline of an MRI apparatus to which the present invention is applied. This MRI apparatus comprises a magnet 101 for generating a static magnetic field, a magnetic field gradient coil 102 for generating magnetic field gradient in the static magnetic field generated by the magnet 101, and a probe 107 for irradiating a radio frequency magnetic field pulse (henceforth referred to as RF pulse) on a test subject 103 and detecting nuclear magnetic resonance signals (echoes) generated by the test subject 103. The test subject (for example, living body) 103 is placed on a bed (table) in the space of the static magnetic field generated by the magnet 101.

The magnetic field gradient coil 102 is connected to a magnetic field gradient power supply 105. The probe 107 is connected to a radio frequency magnetic field generator 106 or a receiver 108 via a switching unit not shown in the drawing. The magnetic field gradient power supply 105, the radio frequency magnetic field generator 106, and the receiver 108 operate according to commands transmitted from a sequencer 104 and generate a magnetic field gradient and a radio frequency magnetic field, respectively. An RF pulse is thereby applied on the test subject 103 via the probe 107, and at the same time, the magnetic field gradient pulses for giving positional information such as slice selection and phase encoding to echo signals are applied by the magnetic field gradient coil 102. Signals generated by the test subject 103 are received by the probe 107, and detection is performed by the receiver 108. Frequency as the reference of the detection (henceforth referred to as detection reference frequency) is set by the sequencer 104. The detected signals are sent to a computer 109 and subjected to signal processing such as image reconstruction therein. The results are displayed on a display 110. The detected signals and measurement conditions can be memorized in a storage medium 111 as required.

The sequencer 104 is a means for controlling operation of each means, and it controls each means so that each means should operate at preliminarily programmed timing and intensity. Among the programs, those describing timings and intensities of the radio frequency magnetic field, magnetic field gradient and signal reception are called pulse sequences. In the MRI apparatus of this embodiment, a GrE type pulse sequence is stored, and imaging mode for measuring echoes required for image reconstruction and non-imaging mode for obtaining a steady state of nuclear magnetization prior to the imaging mode are executed. In such an operation, the flip angle of the RF pulse used in the imaging mode is controlled on the basis of the flip angle used in the non-imaging mode. Specific embodiments of the control will be described later.

Various GrE type pulse sequences are known, and an arbitrary GrE type pulse sequence can be employed depending on a part or tissue as an object of imaging. Specific examples thereof are shown in FIGS. 2 and 3. The pulse sequence shown in FIG. 2 is a fundamental GrE type pulse sequence. As shown in (a), a slice magnetic field gradient pulse 201 in the z-axis direction is applied, and a radio frequency magnetic field (RF) pulse 202 is irradiated at the same time to induce magnetization in a certain slice in an objective material. Then, after a slice-rephase magnetic field gradient pulse 203, a phase encoding magnetic field gradient pulse 204 for adding positional information for the phase encoding direction (y-axis direction) to the phase of magnetization, and a read-out magnetic field gradient 205 for dephase are applied, a magnetic resonance signal (echo) 207 is measured while applying a read-out magnetic field gradient pulse 206 for adding positional information for the read-out direction (x). The above-described procedure from the application of the slice magnetic field gradient pulse to the echo measurement is repeated in the repetition time TR while changing intensity of the phase encoding magnetic field gradient pulse 204 (phase encoding amount, kp) for each time to measure echoes required to obtain one image. The echoes are arranged on a k-space as shown in (b), and an image is reconstructed by two-dimensional inverse Fourier transform. This pulse sequence has a characteristic of providing a T1 (longitudinal relaxation time)-enhanced image.

The pulse sequence shown in FIG. 3 is a pulse sequence known as a phase compensation type pulse sequence, in which magnetic field gradient pulses 208, 209 and 210 for making the time integration value of the magnetic field gradient for each axis zero are added to the pulse sequence shown in FIG. 2. This pulse sequence provides contrast reflecting T2 (transverse relaxation time)/T1, and favorable contrast of tissues and blood, and therefore it is suitable for morphological and functional diagnoses of the heart or morphological diagnosis of the abdominal part.

Besides the pulse sequences shown in FIGS. 2 and 3, a radial scan in which read-out gradients along two axes are used in combination and a 3D-GrE pulse sequence using phase encoding also for slice axis may also be used.

In the imaging mode, the magnetic resonance signal (echo) 207 is measured while the magnetic field gradient pulse 206 for the read-out direction (x) is applied as shown in the drawing. On the other hand, in the non-imaging mode, the phase encoding magnetic field gradient is not used, and the excitation pulse 202 is irradiated for the same repetition time TR as that used for the imaging mode without measuring the echo.

Hereafter, control of the flip angle of the RF pulse in the non-imaging mode and the imaging mode will be explained.

Configuration of the sequencer 104 and procedure for pulse sequence control are shown in FIGS. 4, (a) and (b). As shown in the drawing, the control performed by the sequencer 104 consists of timing control 401 for controlling timings of application of the magnetic field pulses and measurement of echo according to the pulse sequence described above, mode control 402 for switching the non-imaging mode and the imaging mode, GC control 403 for controlling intensity of the magnetic field gradient pulse, RF pulse control 404 for controlling frequency and intensity of the RF pulse, and so forth. Control of the flip angle is performed as a part of the RF pulse control 404. The procedures of these controls are incorporated into the sequencer 104 as programs, and required conditions and parameters can be inputted by using an input means (not shown) provided on the computer 109.

For example, after the imaging method (pulse sequence) and parameters thereof are set by using the input means (step 411), the maximum values, modulation widths, modulation patterns, and so forth of the flip angle in the non-imaging mode and the imaging mode may be set by a user as conditions for control of the flip angle (step 412). Upon the imaging is started, the radio frequency magnetic field generator 106 controls amplitude of the radio frequency magnetic field in response to the timing control 401 and the RF control 404 by the sequencer 104, and generates a radio frequency magnetic field pulse providing a predetermined flip angle from the probe 107 (step 413). Echo signals obtained by the above procedure are corrected as required and used to perform image reconstruction (step 414).

The control of the flip angle in the non-imaging mode will be explained first. In the non-imaging mode, the flip angle of the RF pulse may be constant or changed from the viewpoint of image contrast. However, the maximum value of the flip angle used in the non-imaging mode determines the upper limit of the flip angle used in the imaging mode. When the flip angle is modulated in the non-imaging mode, it is preferred that the flip angle immediately before the shift to the imaging mode should be the maximum value thereof. Thereby, in the imaging mode in which the flip angle is defined by the maximum value, sufficient image contrast can be secured. In addition, it is known that if the flip angle is modulated in the non-imaging mode so as to become larger from the first half to the second half, imaging can be entered to the imaging mode in a short time with a small number of repetition times as small as several tens of times. Therefore, the modulation which makes the flip angle maximum immediately before the entry to the imaging mode also effective for reduction of SAR.

In the imaging mode, the flip angle is changed in a range of values not larger than the maximum value of the flip angle used in the non-imaging mode. The modulation of the flip angle may be performed as, for example, monotone decreasing or a combination of monotone decreasing and monotone increasing. Although it may be linear or nonlinear, it preferably consists of substantially continuous modulation. That is, flip angles for contiguous echoes preferably change substantially continuously. Moreover, although it is preferred that the flip angle immediately after the start of the imaging mode is the same as the last flip angle in the non-imaging mode, they may be different from each other.

Embodiments of the modulation pattern are shown in each (a) in FIGS. 5 to 7. In these drawings, the vertical axes represent the flip angle and the horizontal axes represent number of repetition. Results of imaging in these embodiments are shown in (b) to (d). In the examples shown in the drawings, imaging is performed by using the phase compensation type two-dimensional pulse sequence shown in FIG. 3 as the pulse sequence with TR/TE=5/2.5 ms, repetition number (number of TR) in the non-imaging mode of 150, field of view of 26 cm, and matrix size of 128×128 as imaging parameters, and successively changing phase encoding kp from −64 to +63 for every TR. As the test subject, four kinds of test subjects 511 to 514 showing different T1/T2 values are used. The T1/T2 values of the test subjects are 800 ms/200 ms (511), 800 ms/100 ms (512), 400 ms/200 ms (513), and 400 ms/100 ms (514). In the drawings, each (b) shows a contrast profile of image of the test subject, each (c) shows image, each (d) shows intensity at the line 520, and 521 indicates edge of the test subject.

Further, for comparison, profiles and images for the cases that the flip angle is maintained to be constant in the non-imaging mode and the imaging mode (the flip angle is 60 degrees in the pattern D, and 30 degrees in the pattern E), and a profile and an image for the case that the flip angle is changed in the imaging mode so that the flip angle is larger than the flip angle used in the non-imaging mode (pattern F) are shown in FIG. 8.

In the embodiment shown in FIG. 5, (a), the flip angle is maintained to be constant in the non-imaging mode 501 (60 degrees in the example shown in the drawing), and gradually decreased in the imaging mode 502 from the flip angle used in the non-imaging mode 501 as the upper limit. In the example shown in the drawing, the flip angle is decreased from 60 degrees to 30 degrees according to a half cycle of a sine function. Image contrast of the image obtainable in this embodiment scarcely changes compared with that obtainable by the imaging performed by maintaining the flip angle to be 60 degrees (pattern D in FIG. 8), and substantially comparable image contrast can be obtained. On the other hand, SAR decreases by 41% compared with that obtainable with the pattern D of FIG. 8. By this SAR reduction effect, imaging with less influence on human body can be realized. When a phase compensation type pulse sequence is used, in particular, SAR reaching 4.7 W/kg in an apparatus using a magnetic field of 3 Teslas, which exceeds the reference value, can be reduced to 2.77 W/kg by applying this embodiment, and it becomes possible to perform such imaging, which has so far been impossible.

In the embodiment shown in FIG. 6, (a), the flip angle is maintained to be constant in the non-imaging mode 601, and changed in the imaging mode 602 in a range of angles not larger than the flip angle used in the non-imaging mode 601, as in the case shown in FIG. 5, (a). However, in the imaging mode 602 of this embodiment, the flip angle is not monotonically decreased during the measurement of total phase encoding, but changed by a combination of monotone decreasing and monotone increasing. In the modulation pattern A, the angle is decreased to 30 degrees from 60 degrees and then increased to 60 degrees according to one cycle of a sign function. Further, in the modulation pattern B, the modulation pattern A is repeated twice during the measurement of total phase encoding. In the modulation pattern C, the modulation pattern is repeated 1.5 times, and then the angle is fixed to 30 degrees during the measurement of total phase encoding. It can be seen that image contrast comparable to that obtainable in the case where the flip angle is fixed to 60 degrees (the pattern D of FIG. 8) can be obtained in all the cases where the modulation pattern A to C are used. The SAR reduction rates in the imaging mode are 41% with the patterns A and B and 49% with the pattern C based on that observed with the pattern D of FIG. 8. The rate obtainable with the pattern C is slightly higher, since the flip angle is fixed to 30 degrees in the second half.

Moreover, from the result obtainable with the modulation pattern A, it can be seen that equivalent image contrast can be obtained even with a small flip angle at the time of measurement in the low phase encoding region 603, and thus the relation between the phase encoding and the flip angle scarcely affects image contrast. On the other hand, as in the modulation pattern F shown in FIG. 8, if the flip angle is fixed to 30 degrees in the non-imaging mode 811, and the flip angle is changed so as to be 60 degrees at the time of measurement in the low phase encoding region 813 in the imaging mode 812, image contrast differs from that obtainable with the pattern D (constant angle of 60 degrees), and is close to the contrast obtainable with the pattern E (fixed to 30 degrees). From this result, it can be seen that image contrast is strongly affected by a steady state formed in the non-imaging mode, and is not dependent so much on the flip angle in the imaging mode, and therefore, in order to reduce SAR, it is preferable to use an angle not larger than the flip angle used in the non-imaging mode as the flip angle for the imaging mode.

In the modulation pattern shown in FIG. 7, (a), the flip angle is modulated also in the non-imaging mode 701. Degree of the modulation is small in the first half, and made larger at a later point in the second half. Like the profile shown in FIG. 5, (a), the flip angle used in the imaging mode 702 is changed so that it should not be larger than the maximum flip angle used in the non-imaging mode 701. It can be seen that, also in this embodiment, image contrast is comparable to that obtainable with the pattern D of FIG. 8 as shown in (b) and (c). In this embodiment, the SAR reduction effect in the imaging mode is the same as that in the case of FIG. 5, (a). However, in this embodiment, since modulation is also performed in the non-imaging mode, the imaging mode can be started after a short period of time with a small number of repetition as small as about several tens of times, and therefore SAR can further be reduced. In the profile shown in FIG. 7, (a), any of the modulation patterns A, B and C shown in FIG. 6, (a) may be used as the modulation pattern for the imaging mode 702, and the same effect can be obtained.

Although the aforementioned flip angle modulation pattern can be arbitrarily determined in consideration of SAR, reduction rate thereof, image contrast, and so forth, when multiple images are continuously obtained in the imaging mode, preferred is a pattern in which, at the end of one time of imaging, the flip angle approaches the flip angle at the beginning of the imaging, as the modulation patterns A and B shown in FIG. 6. A modulation method suitable for such continuous imaging is shown in FIG. 9. In the example shown in the drawing, the flip angle is fixed (60 degrees) in the non-imaging mode 901, and changed in the imaging mode 902 according to the same modulation pattern as the modulation pattern B shown in FIG. 6 repeated 5 times to continuously obtain five images. In the drawing, change of the flip angle over the number of times of repetition is shown in (a), and the superimposed profiles of the five images are shown in (b). As shown in (b), the profiles of five images are substantially the same, and indicate that contrast is stable in the images continuously obtained. Image contrast comparable to that obtained in FIG. 4 is also obtained for them. When multiple images are continuously obtained as described above, by making flip angles for the start and the end of the procedure for obtaining each image closer to each other, it becomes possible to decrease SAR without degrading image contrast and stably obtain images. The SAR reduction rate obtained with the modulation pattern of FIG. 9 is 41%, which is the same as that obtained with the modulation pattern B shown in FIG. 6.

Embodiments of modulation patterns for flip angle modulation are explained above together with the effect thereof in an imaging method using a phase compensation type GrE pulse sequence, which imposes severer SAR conditions. However, the effect of the aforementioned flip angle modulation is not limited to a phase compensation type GrE pulse sequence, and is commonly obtained with GrE type pulse sequences.

Image reconstruction will be explained below. The computer 109 performs operation including the Fourier transform and so forth using echoes measured in the imaging mode to reconstruct an image. As shown by the profiles and images shown in FIGS. 5 to 7, image contrast which is comparable to that obtainable with the flip angle fixed to a certain value can be obtained by the MRI apparatus of the present invention. However, if the flip angle is modulated in the imaging mode, intensity of echo is also modulated substantially in proportion to the flip angle. Therefore, according to the relation between the flip angle and the phase encoding, edges of image may be enhanced or images become obscure. For example, in the image shown in FIG. 5, (c), edges 521 of the test subject shows intensity of the same degree as that of intermediate portions as shown in (d), whereas in the image shown in FIG. 6, A, (c), upper and lower edges 621 of the test subject are enhanced. Further, in FIGS. 6, B and C, the upper and lower edges of the test subject are unsharpened. In order to avoid such a phenomenon, echoes are corrected at the time of image reconstruction by calculating a product of the reciprocal of the flip angle fa and each echo (signal value) as represented by the following equation (1).

$$s_i' = 1/fa \times s_i \ (i=1, \ldots, n) \quad (1)$$

In the equation, $s_i$ and $s_i'$ are values obtained at an echo sampling point before and after the correction, respectively, n is a number of sampling points, and fa is a flip angle of excitation pulse immediately before measurement of $s_i$.

By performing reconstruction by Fourier transform of the corrected echoes, it becomes possible to obtain a favorable image. However, intensity of each echo is not strictly proportional to the flip angle. Therefore, in order to perform strict intensity correction, it is preferable to measure relation between the flip angle and echo intensity, for example, by using a reference echo, and correct the echo based on it.

As another embodiment, an MRI apparatus provided with a means for correction based on reference echo will be explained below. The configuration of the apparatus of this embodiment is the same as that of the aforementioned embodiment, and a modulation pattern such as those shown in FIGS. 5 to 7 is employed as a flip angle modulation pattern for RF pulse also in this embodiment like the aforementioned embodiment. However, in this embodiment, as shown in FIG. 10, a step 1003 of measuring a reference echo for correction of influence of flip angle modulation is inserted between the non-imaging mode 1001 and the imaging mode 1002.

The measurement of reference echo is performed by, for example, executing the imaging mode once in a state that phase encoding is made zero for all the echoes to measure a series of echoes (reference echoes) (1003). The measured reference echoes are saved in the storage medium 111, and used for correction of the echoes measured in the imaging mode.

In the image reconstruction, intensity A of each reference echo is first calculated in accordance with the following equation (2). The intensity A of reference echo is, for example, an integration value of absolute value of reference echo. Then, a product of reciprocal of the intensity of reference echo (1/A) and each echo for reconstruction is calculated as an corrected echo in accordance with the equation (3).

$$A = \Sigma |ri| \ (i=1, \ldots, n) \quad (2)$$

$$si' = 1/A \times s_i \quad (3)$$

In the equations (2) and (3), ri is a value of reference echo obtained at a sampling point, $s_i$ and $s_i'$ are values obtained at an echo sampling point before and after the correction, respectively, and n is a number of sampling points. Further, A is intensity of a reference echo, and it is an integration value of absolute value of the reference echo in this case.

By performing reconstruction by Fourier transform of the corrected echoes, it is possible to obtain a favorable image.

According to this embodiment, by changing the flip angle of the RF pulse in the imaging mode in a range of values not larger than the value determined by the flip angle used in the non-imaging mode like the first embodiment, SAR can be reduced, and a favorable image not only free from degradation of image contrast, but also free from influence of flip angle modulation such as unsharpness and enhancement of edges can be obtained.

EXPLANATION OF NUMERAL SYMBOLS

Figure 1:
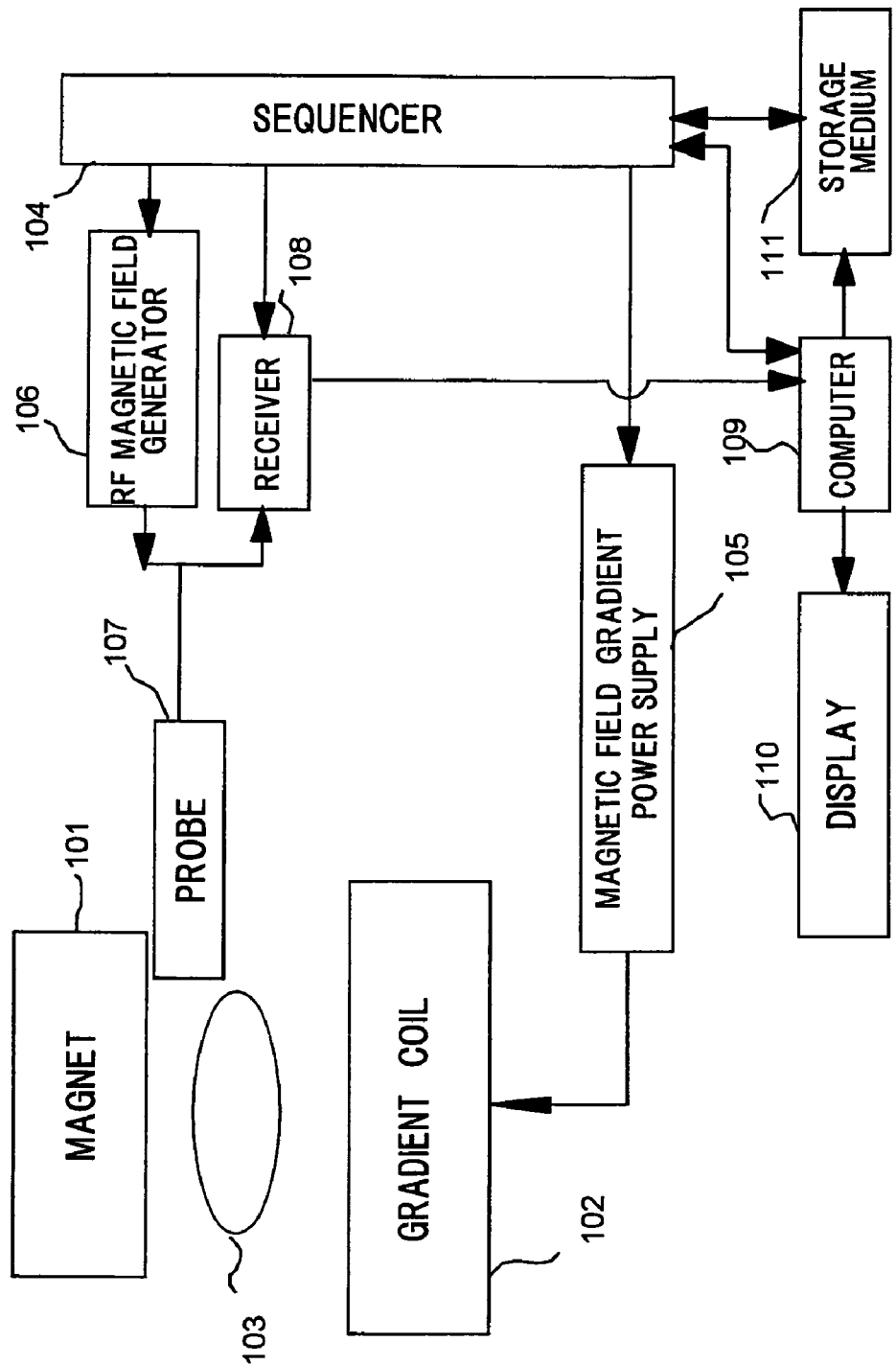
FIG. 1 A block diagram showing total configuration of an MRI apparatus to which the present invention is applied.
Figure 2:
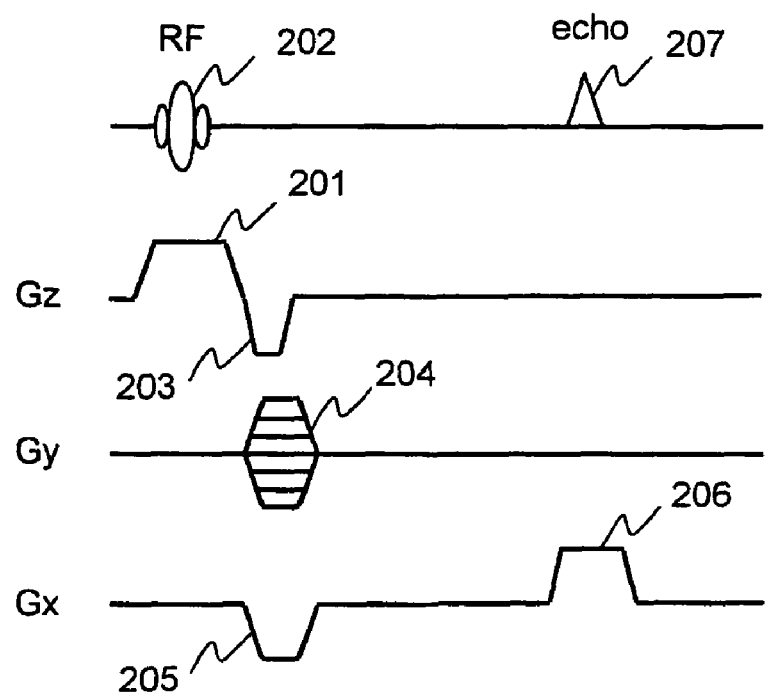
FIG. 2 A drawing showing a pulse sequence for the gradient echo method and k-space.
Figure 2:
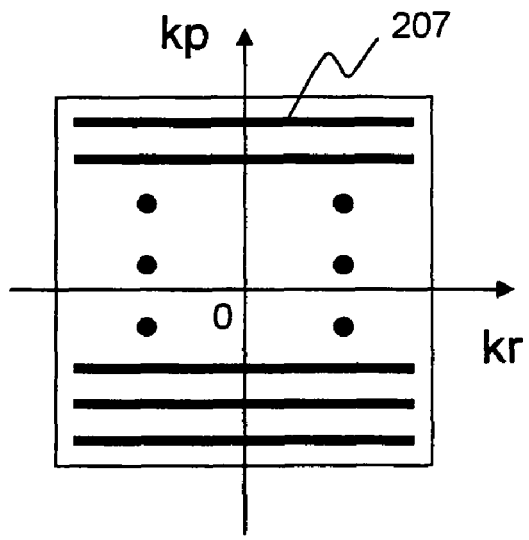
Figure 3:
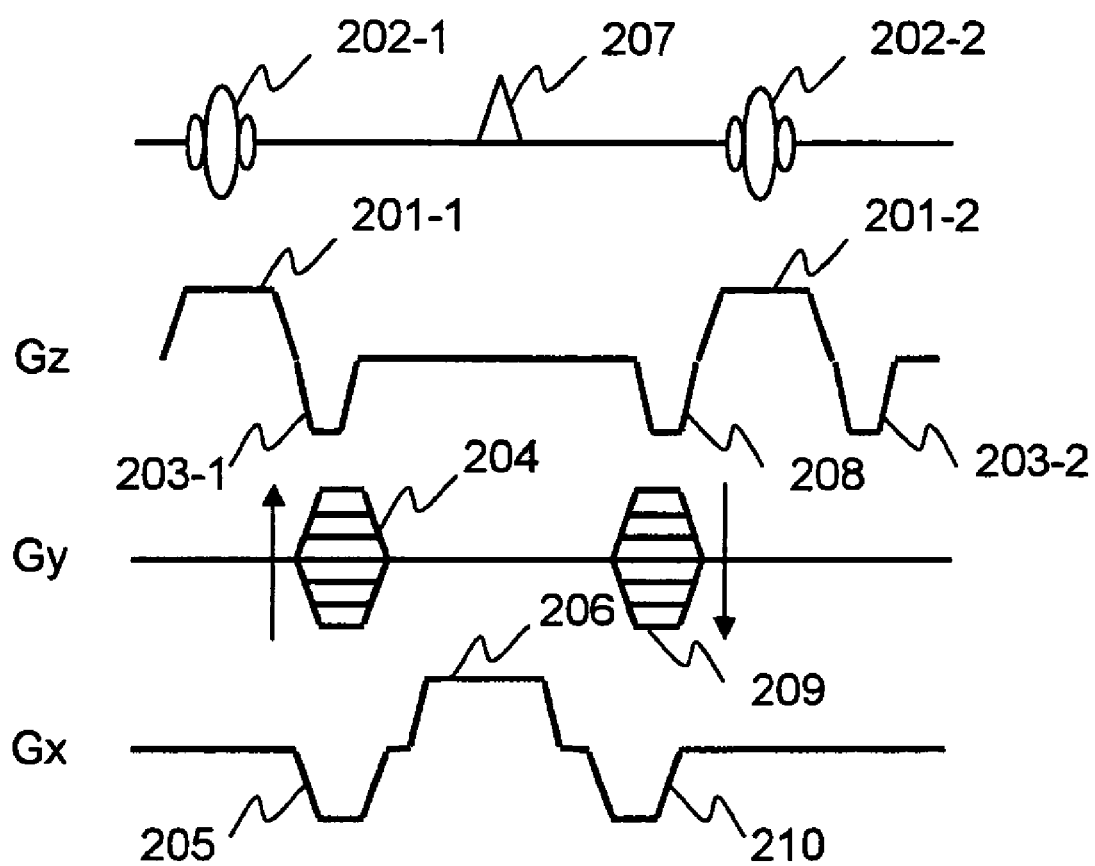
FIG. 3 A drawing showing a pulse sequence for the phase compensated type gradient echo method.
Figure 4:
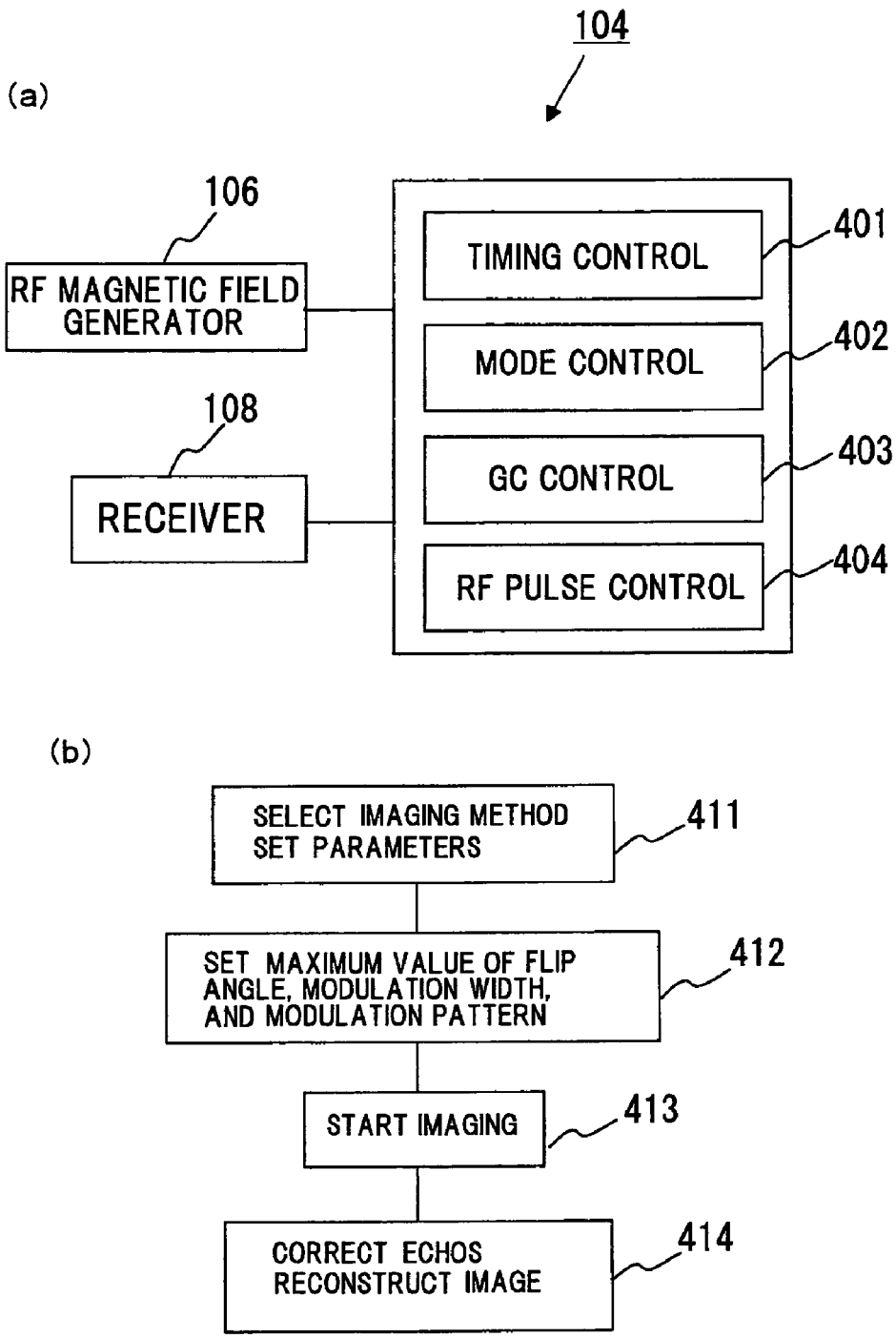
FIG. 4 A drawing showing details of control by a sequencer.
Figure 5:
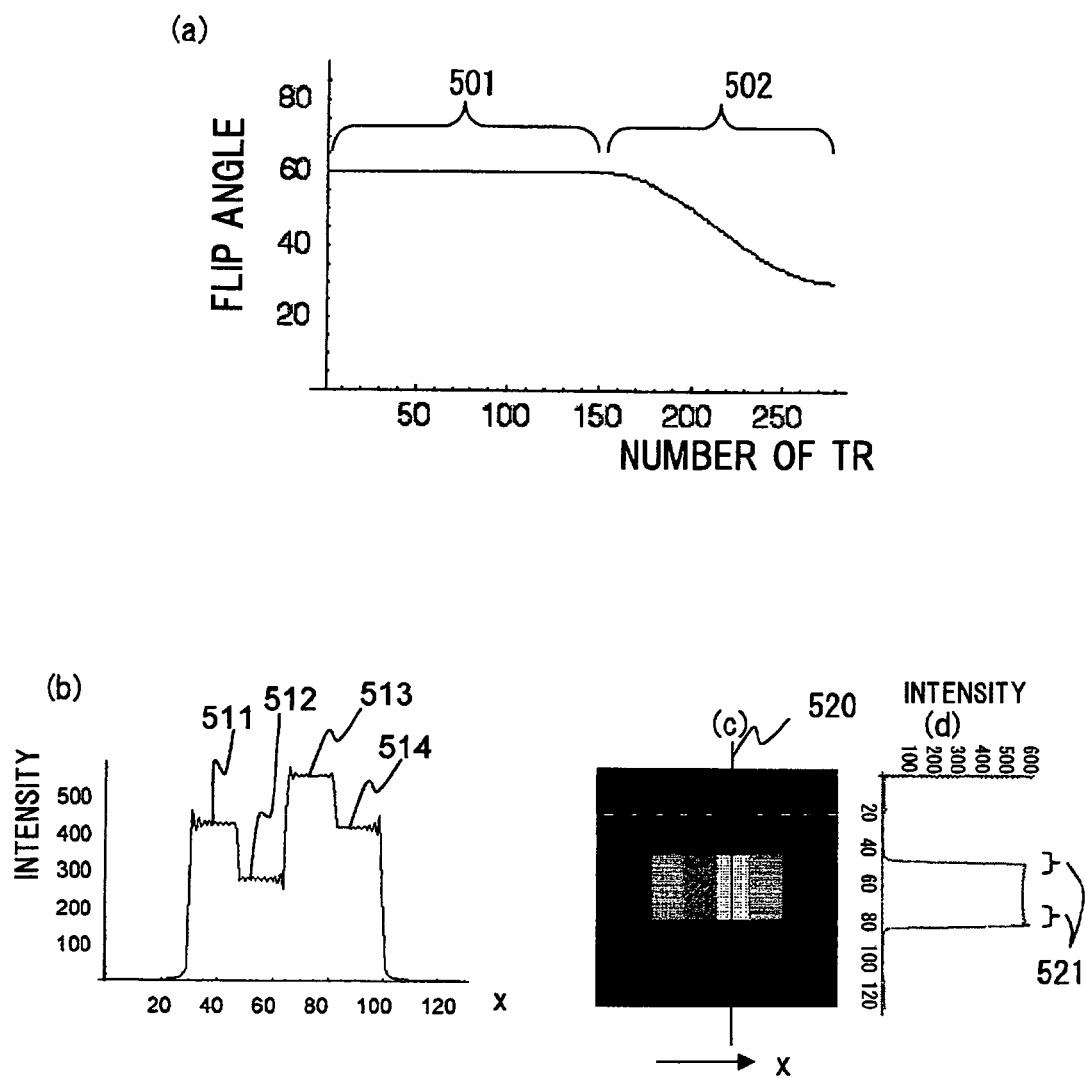
FIG. 5 A drawing showing flip angle and imaging results for one embodiment of the present invention.
Figure 6:
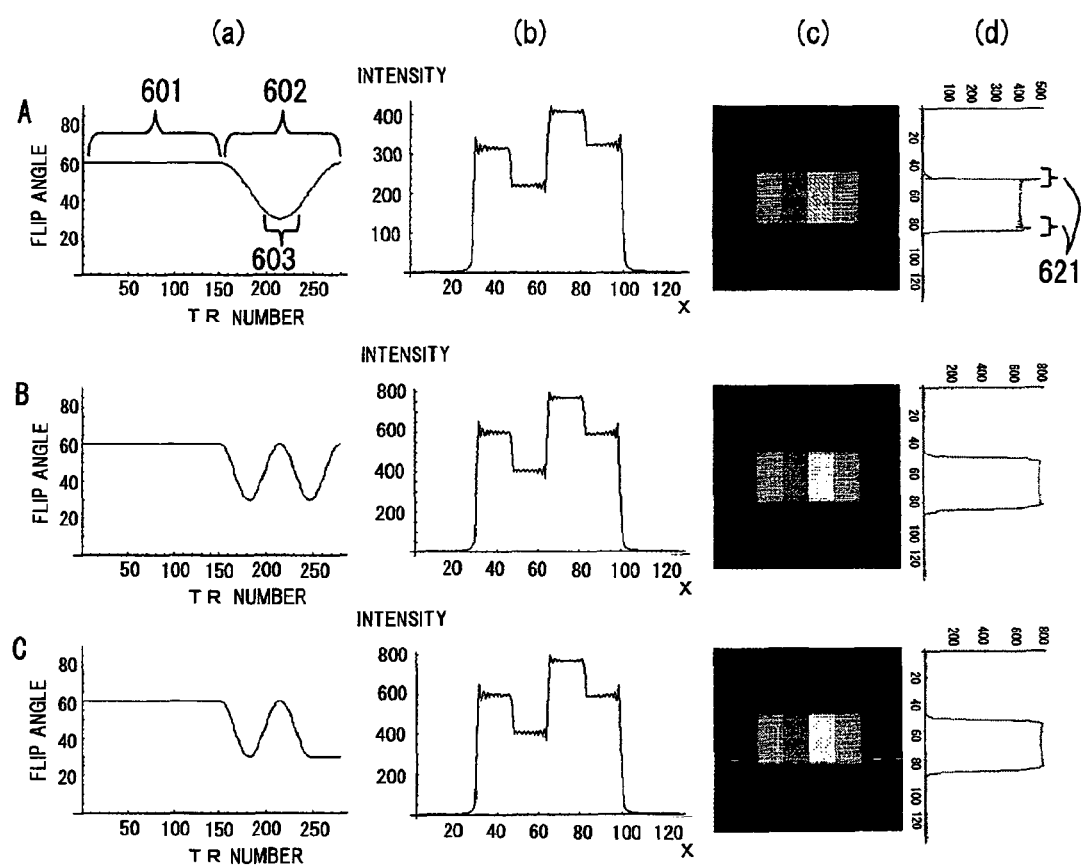
FIG. 6 A drawing showing flip angles and imaging results for another embodiment of the present invention.
Figure 7:
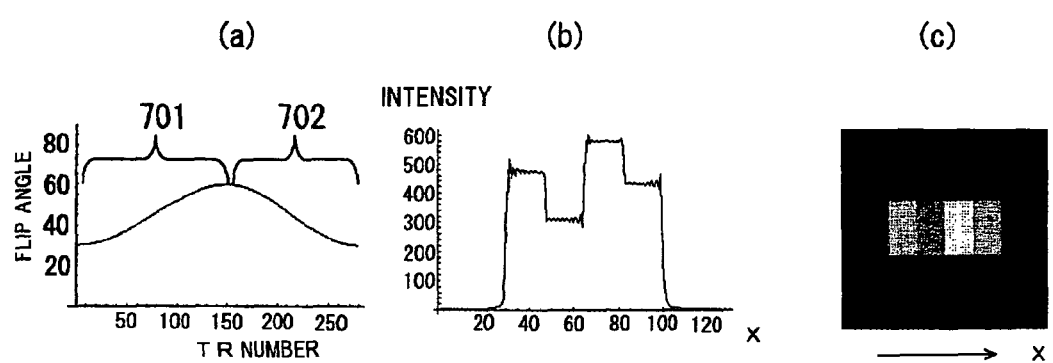
FIG. 7 A drawing showing flip angle and imaging result for another embodiment of the present invention.
Figure 8:
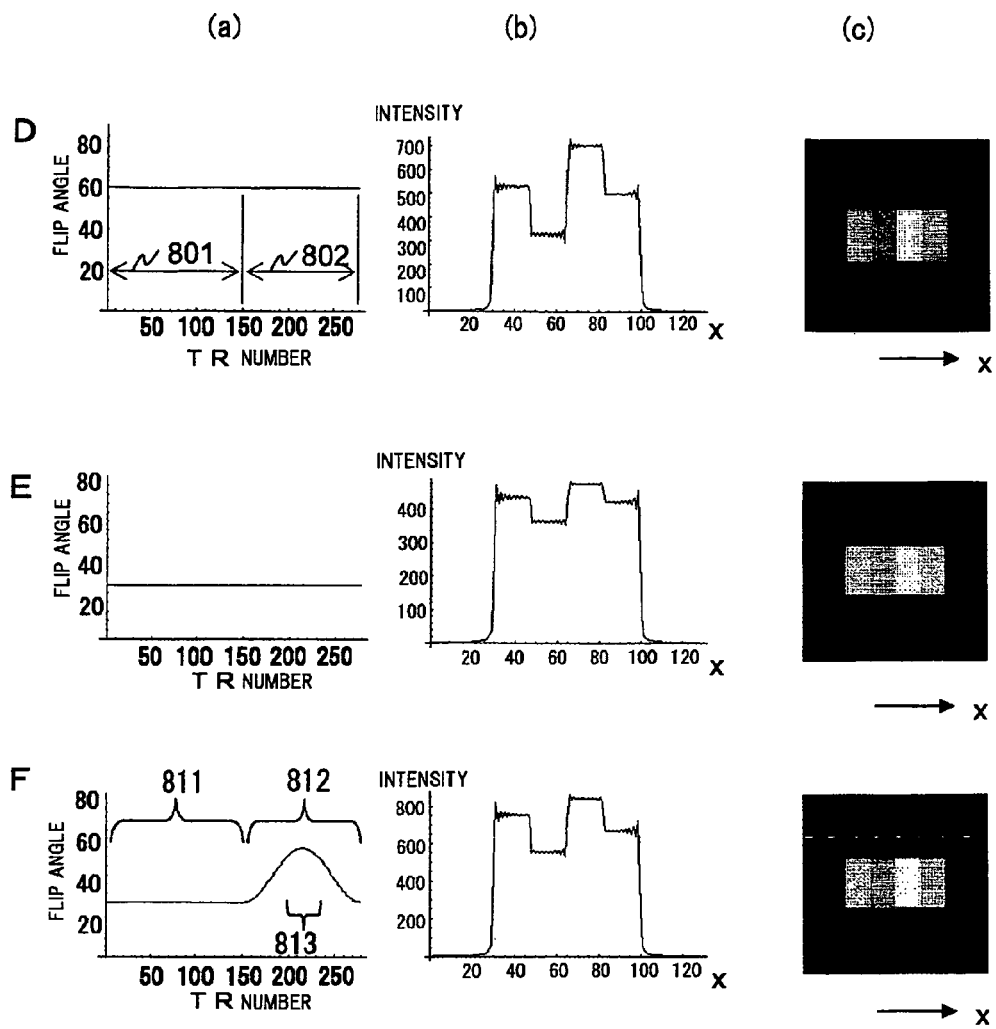
FIG. 8 A drawing showing flip angles and imaging results for a conventional imaging method.
Figure 9:
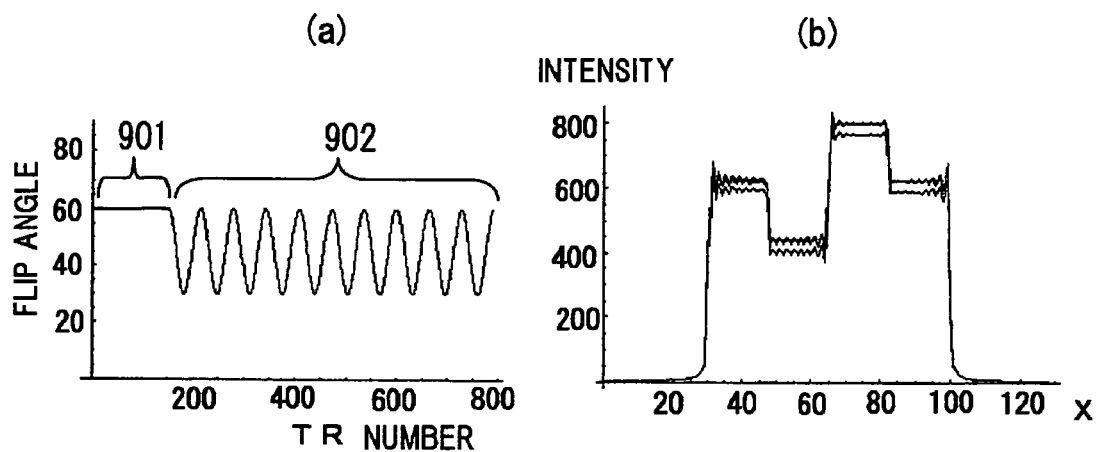
FIG. 9 A drawing showing flip angle and imaging result for another embodiment of the present invention.
Figure 10:
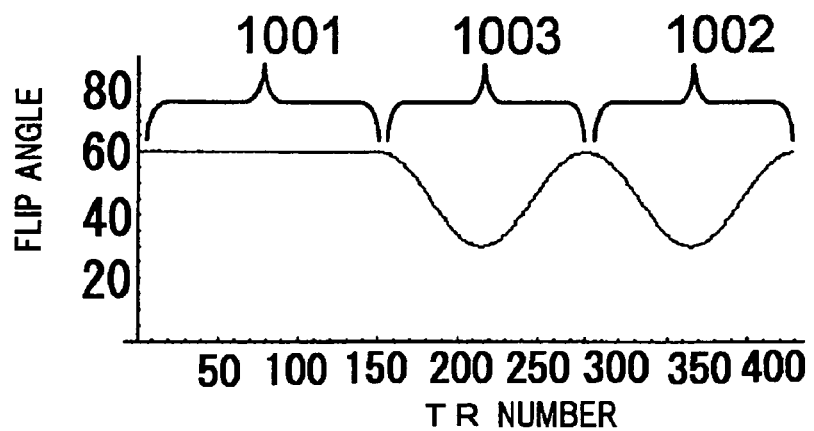
FIG. 10 A drawing for explanation of imaging according to the second embodiment of the present invention.

101 . . . Magnet for generating static magnetic field, 102 magnetic field gradient coil, 103 . . . test subject, 104 . . . sequencer, 105 . . . magnetic field gradient power supply, 106 . . . radio frequency magnetic field generator, 107 . . . probe, 108 . . . receiver, 109 . . . computer, 110 . . . display, 111 . . . storage medium.

The invention claimed is:

1. A magnetic resonance imaging apparatus comprising a means for generating a static magnetic field, a means for generating a magnetic field gradient to be superimposed on the static magnetic field, a means for irradiating an excitation RF pulse on a test subject placed in the static magnetic field, a means for detecting nuclear magnetic resonance signals emitted from the test subject, a means for reconstructing an image from the nuclear magnetic resonance signals, and a means for controlling the means for irradiating an excitation RF pulse and the means for detecting nuclear magnetic resonance signals so as to execute a non-imaging mode in which a nuclear magnetic resonance signal is not measured after irradiation of an excitation RF pulse, and an imaging mode in which a nuclear magnetic resonance signal is measured after irradiation of an excitation RF pulse, wherein:

the means for irradiating an excitation RF pulse changes flip angle of nuclear magnetization in the imaging mode in a range of values not larger than a certain value defined by a flip angle of nuclear magnetization used in the non-imaging mode;

the means for irradiating an excitation RF pulse substantially continuously modulates flip angle of nuclear magnetization in the imaging mode; and the means for irradiating an excitation RF pulse modulates flip angle of nuclear magnetization in one time of imaging in the imaging mode so that flip angle at the beginning of the imaging and flip angle at the end of the imaging should be the same or substantially the same.

2. The magnetic resonance imaging apparatus according to claim 1, wherein:

the means for irradiating an excitation RF pulse changes flip angle of nuclear magnetization in the imaging mode in a range of values not larger than the maximum value of flip angle of nuclear magnetization used in the non-imaging mode.

3. The magnetic resonance imaging apparatus according to claim 1, wherein:

the means for controlling executes the non-imaging mode and the imaging mode successively, and the means for irradiating an excitation RF pulse changes flip angle of nuclear magnetization in the imaging mode in a range of values not larger than a certain value that is the last flip angle of nuclear magnetization used in the non-imaging mode.

4. The magnetic resonance imaging apparatus according to claim 1, wherein:

the means for irradiating an excitation RF pulse modulates flip angle of nuclear magnetization according to a monotonically decreasing function in one time of imaging in the imaging mode.

5. The magnetic resonance imaging apparatus according to claim 1, wherein:
the means for controlling executes two or more times of imaging in the imaging mode.

6. The magnetic resonance imaging apparatus according to claim 1, wherein:
the means for controlling executes imaging in the non-imaging mode and the imaging mode by using a gradient echo type pulse sequence.

7. The magnetic resonance imaging apparatus according to claim 6, wherein:
when the means for controlling executes imaging by using the gradient echo type pulse sequence, time integration value of magnetic field gradient applied within a term between contiguous two times of RF pulse irradiation is made to be zero.

8. The magnetic resonance imaging apparatus according to claim 1, wherein:
the means for reconstructing an image includes a means for correcting the nuclear magnetic resonance signals measured in the imaging mode according to flip angle of the excitation RF pulse used in order to generate the nuclear magnetic resonance signals.

9. The magnetic resonance imaging apparatus according to claim 1, wherein:
the means for reconstructing an image corrects signal strength with a reciprocal of flip angle.

10. The magnetic resonance imaging apparatus according to claim 1, wherein:
the means for controlling executes, after the non-imaging mode, a reference imaging mode in which nuclear magnetic resonance signals are measured at phase encoding of 0 after the irradiation of excitation RF pulse, and the means for reconstructing an image corrects the nuclear magnetic resonance signals measured in the imaging mode using reference signals obtained by the reference imaging mode.

11. The magnetic resonance imaging apparatus according to claim 1, wherein:
the means for irradiating an excitation RF pulse modulates flip angle of nuclear magnetization in one time of imaging in the imaging mode so that flip angle should be the same or substantially the same as the flip angle at the beginning of the imaging, at least once in the imaging.

12. A resonance imaging apparatus comprising a means for generating a static magnetic field, a means for generating a magnetic field gradient to be superimposed on the static magnetic field, a means for irradiating an excitation RF pulse on a test subject placed in the static magnetic field, a means for detecting nuclear magnetic resonance signals emitted from the test subject, a means for reconstructing an image from the nuclear magnetic resonance signals, and a means for controlling the means for irradiating an excitation RF pulse and the means for detecting nuclear magnetic resonance signals so as to execute a non-imaging mode in which a nuclear magnetic resonance signal is not measured after irradiation of an excitation RF pulse, and an imaging mode in which a nuclear magnetic resonance signal is measured after irradiation of an excitation RF pulse, wherein:
the means for irradiating an excitation RF pulse changes flip angle of nuclear magnetization in the imaging mode in a range of values not larger than a certain value defined by a flip angle of nuclear magnetization used in the non-imaging mode, and modulates flip angle of nuclear magnetization in one time of imaging in the imaging mode so that flip angle at the end of the imaging should be smaller than flip angle at the beginning of the imaging, substantially continuously in the imaging mode.

* * * * *